United States Patent
Brungart

(10) Patent No.: US 6,463,316 B1
(45) Date of Patent: Oct. 8, 2002

(54) DELAY BASED ACTIVE NOISE CANCELLATION FOR MAGNETIC RESONANCE IMAGING

(75) Inventor: Douglas S. Brungart, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/544,222

(22) Filed: Apr. 7, 2000

(51) Int. Cl.$^7$ ................................................ A61B 5/05
(52) U.S. Cl. .................... 600/410; 600/418; 600/421; 381/71.1; 381/72
(58) Field of Search ............................... 600/410, 411, 600/418, 421; 381/71, 72

(56) References Cited

U.S. PATENT DOCUMENTS

| | | | |
|---|---|---|---|
| 4,933,981 A | * | 6/1990 | Lederer |
| 5,133,017 A | * | 7/1992 | Cain et al. |
| 5,262,884 A | | 11/1993 | Buchholz .................... 359/151 |
| 5,313,945 A | * | 5/1994 | Friedlander |
| 5,427,102 A | * | 6/1995 | Shimode et al. |
| 5,692,056 A | | 11/1997 | Gardner .................... 381/71.2 |
| 5,821,748 A | | 10/1998 | Gatehouse .................. 324/318 |
| 5,877,732 A | | 3/1999 | Ziarati .......................... 345/8 |
| 5,990,680 A | | 11/1999 | Mansfield ................... 324/318 |

* cited by examiner

Primary Examiner—Marvin M. Lateef
Assistant Examiner—Talaya James
(74) Attorney, Agent, or Firm—Gina S. Tollefson; Gerald B. Holins; Thomas L. Kundert

(57) ABSTRACT

System and method for actively canceling the acoustic noise generated by changes in the electric current within the gradient coils of a magnetic resonance imager based on the finding that the acoustic noise in the magnetic resonance imager is highly periodic but that the period of the magnetic resonance imager noise changes substantially during a scan. The acoustic noise signal is measured at the ears of a patient undergoing a magnetic resonance imaging, delayed by a variable number of samples and the resulting signal is subtracted from the acoustic noise signal. Magnetic resonance imaging noise cancellation occurs at the level of 20 decibels or more.

18 Claims, 9 Drawing Sheets

DELAY BASED ACTIVE NOISE CANCELLATION FOR MAGNETIC RESONANCE IMAGING

RIGHTS OF THE GOVERNMENT

The invention described herein may be manufactured and used by or for the Government of the United States for all governmental purposes without the payment of any royalty.

BACKGROUND OF THE INVENTION

The field of the invention is noise minimization for magnetic resonance imaging and more specifically to delay based active noise cancellation for magnetic resonance imaging.

Magnetic resonance imagers (MRI) are extremely valuable tools for medical scanning. MRI systems are able to identify different types of tissue within the human body by placing the tissue in a strong magnetic field generated by a superconducting magnet and exciting the tissue (specifically the spin states of the molecules within the tissue) with a pulse of RF energy, and then measuring the electromagnetic emissions of the tissue as its spin states relax to the rest position. The MRI scanner is able to map the spatial locations of the different types of tissue by creating gradients in the magnetic field that change the response of the tissue as a function of spatial location within the body.

Researchers have long recognized the severity of the noise problem in MRI scanners and that they impair patient comfort and contribute to patient anxiety. Numerous studies have examined the acoustic characteristics of these noise fields. The MRI sound is created by "knocking" of the gradient coils. The gradient coils in the MRI are oriented orthogonally to the field of the static magnet. During the imaging, the current in these coils is turned on and off at 5–10 ms intervals. Each time the coil current is switched on in the magnetic field, a force is created that is orthogonal to both the direction of the current and the magnetic field (i.e. radially outward). This sudden force on the gradient coil causes it to "knock" against its mounting, creating acoustic noise. The characteristics of the noise are therefore directly related to the gradient pulse sequence used in the scan, and will vary substantially according to the scan performed. Studies have examined the acoustic characteristics of the noise fields by placing a condenser microphone inside the MRI. These studies, after verifying that the microphone was not effected by the electromagnetic fields in the scanner, have generally shown that the imager noise in a 1.5 Telsa MRI scanner is approximately 100–105 dB SPL during a relatively noisy MRI scan. More recent studies indicate that the peak noise level in a functional MRI scanner is approximately 118 decibel for a 1.5 Telsa MRI and 134 decibel for a 3.0 Telsa MRI scanner, suggesting that the more powerful MRI systems may be 15 decibel louder than the 1.5 Telsa scanners.

The noise generated by "gradient coil knocking" are disadvantageous for several reasons. First, the noise levels are sufficiently high that they could damage the patient's hearing. Occupational Safety and Health Agency guidelines limit occupational exposure to noise to 30 minutes per day at 105 decibels SPL and to less than 15 minutes per day at 115 decibel SPL. Since MRI scans can take 40 minutes or longer, patients who are scanned without hearing protection may exceed these limitations (particularly in the 3.0 Telsa scanners). The risk of exposure may be even worse in patients taking drugs that enhance the damaging effects of sound, such as aminoglycoside antibiotics. Second, the noise generated by the MRI scanner is annoying to patients and contributes to their anxiety about the MRI scan. It is now common practice to provide patients with pneumatic headphones that attenuate the sound field and mask the imaging noise with music. However, the imaging noise remains clearly audible over this music. Finally, the MRI noise inhibits the use of functional MRI scanners (FMRI) to examine the areas of the brain stimulated by acoustic stimuli. The FMRI compares the activity in the brain with no stimulus to the activity that occurs when the subject is exposed to a stimulus. The fMRI generates such a loud acoustic stimulus that it is impossible to conduct a controlled study of the processing of sound by the brain.

In the past, both passive and active attenuation have been used to mitigate MRI noise. The passive attenuation usually consists either of foam insert ear plugs or ear muffs. Under normal circumstances these systems can provide 20 –30 decibel of attenuation. Commonly these hearing protection devices are combined with a pneumatic-driven system carrying sound to the patient's ears via plastic tubes (similar to the type of headset once commonly used on commercial aircraft). The pneumatic sound system allows the operator to give verbal instructions to the patient or play music, but probably somewhat reduced the passive attenuation of the hearing protection devices. Recently, a noise-attenuating headset has been developed that uses shielded non-magnetic (piezoelectric) electro-acoustic transducers to generate an audio signal inside the MRI without the considerable delays inherent in pneumatic headphones (as sound propagates from the driver unit into the MRI magnet bore through a tube).

Known active MRI attenuation noise cancellation systems include a system that uses a standard pneumatic headset system in which polyethylene tubes carry an acoustic signal from a pneumatic driver unit outside the MRI system to a pair of earmuffs worn by a patient. The pneumatic headset is modified with two additional polyethylene tubes that carry the sound signal inside the earmuff away from the headset to a pair of electret microphones located inside the MRI room. The electret microphones are connected to an electro-optical transducer which carry the earmuff noise signal to the shielded control room via fiber optic cables. A "compensation amplifier" produces an anti-noise signal by filtering the noise signal measured by the microphones and playing this signal back through the pneumatic headphones. An average attenuation of 11.1 decibel was reported for this system.

However, there are a number of issues with this MRI noise-cancellation system which are unresolved. The first limitation involves the frequency spectrum where the noise is canceled. The system is only effective at low frequencies (from 40 Hertz to 500 Hertzl and this is inconsistent with measurements of imager noise which indicate that most of the MRI noise occurs around 1 kiloHertz. Indeed, in a T1 pre-scan, 95% of the acoustic power in the noise signal was in the range from 840 Hertz–1920 Hertz. Thus, it does not appear that this prior art MRI system would be capable of attenuating the MRI scans by 10 dBA. The second issue or limitation with the system is the handling of the large time delays between the acoustic noise signal and its measurement by the electret microphones, and between the generation of the acoustic anti-noise signal by the compensation and its arrival at the listener's ear. Both the measurement and production of sound in the system are limited by the propagation speed of sound. The signal at the patient's ear must travel down the tube before reaching the electret microphones, a distance of at least 5 ft and a delay of at least 5 ms, and the antinoise signal must travel back down the tube before reaching the listener's ears, at distance of perhaps 20 ft and a delay of 20 ms. Thus there is a built in delay in the control loop of this system of at least 20 ms, or 10 periods of a 500 Hz signal. Such a delay would compromise most traditional noise canceling algorithms such as the LMS algorithm.

Another known prior art active MRI noise cancellation system uses non-magnetic microphones located at fixed locations inside the magnet bore to record the error signal, and non-magnetic piezoceramic loudspeakers located at fixed locations to generate the noise cancellation signal. Thus, the system cancels the MRI noise signal at fixed locations inside the MRI, rather than at the locations of the patient's ears. The system uses a two-stage adaptive processing algorithm to generate the noise cancellation signal. The system is capable of reducing acoustic noise by 15–25 dB decibel? We need to be consistent in fast scan sequences and by up to 10 dB in slower "impulsive" scan sequences. However, it should be noted that this cancellation occurs at the locations of the error microphones, and not necessarily at the locations of the patients ears. Consequently, the actual noise attenuation experienced by the patient may be substantially lower.

A third prior art active noise cancellation system includes a feed-forward system in which a reference signal is processed to generate an anti-noise signal played by an electro-acoustic transducer to cancel the MRI noise at the location of error microphones placed inside the MRI near the patients head. The cancellation sound is generated by a loudspeaker located outside the magnet bore and transmitted to the patient's ears through tubes. Using pulse codes, this known prior art system predicts the acoustic noise generated by the MRI before the noise is actually created. This is a tremendous advantage in the active cancellation of MRI noise for two reasons. First, it allows the noise cancellation system to construct a nearly perfect inverse noise waveform a priori without exposure to the current noise generated by the MRI. The system is reactive, and must wait until the characteristics of the noise change before starting to adapt to the new noise. In traditional adaptive noise cancellation system, each time the noise changes the system will cease canceling the noise effectively until the algorithm has time to adapt to the change. In contrast, an active noise cancellation system that uses a priori information from the pulse code sequence can generate a noise cancellation signal before the noise signal is measured by the system and does not have to adapt to changes in the signal.

However, the prior art MRI active-noise-reduction systems have significant drawbacks. Prior art implementations require extensive modification of the MRI system. For example, microphones and loudspeakers must be permanently mounted inside the MRI system or relatively extensive software changes are required. A noise cancellation system that requires modifications to the MRI system is probably not economically feasible for implementation in the large installed base of MRI scanners because of the extreme expense and fragility of the MRI scanners. The costs of modifying the MRI and ensuring its subsequent functionality would dwarf the costs of the hardware involved in the cancellation system.

Additionally, all of the prior art systems have significant technological drawbacks. One prior art system does a good job of canceling the MRI noise at fixed-location microphones inside the scanner, but these microphone locations may not accurately reflect the noise field at the patients ears. Another prior art system requires a linear or well-characterized non-linear transfer characteristic between the pulse currents entering the gradient coils of the MRI and the resulting acoustic noise. This may be an unreasonable expectation.

The present invention some important advantages over these prior systems. The system described herein is based on a completely novel method of active noise control that is derived directly from the acoustic noise characteristics of the MRI system.

SUMMARY OF THE INVENTION

A system and method for actively canceling the acoustic noise generated by changes in the electric current within the gradient coils of a magnetic resonance -imager based on the finding that the acoustic noise in the magnetic resonance imager is highly periodic but that the period of the magnetic resonance imager noise changes substantially during a scan. The acoustic noise signal is measured at the ears of a patient undergoing a magnetic resonance imaging, delayed by a variable number of samples and the resulting signal is subtracted from the acoustic noise signal. Magnetic resonance imaging noise cancellation occurs at the level of 20 decibels or more.

It is therefore an object of the invention to provide an instantaneously adaptable magnetic resonance imaging noise cancellation system.

It is another object of the invention to provide an inherently stable magnetic resonance imaging noise cancellation system.

It is another object of the invention to provide a magnetic resonance imaging noise cancellation system capable of coping with propagation delays.

It is another object of the invention to provide a magnetic resonance imaging system implemented inside an MRI system without modifying the MRI system.

These and other objects of the invention are described in the description, claims and accompanying drawings and are achieved by an improved patient comfort, magnetic resonance imaging noise cancellation system comprising:

a magnetic resonance imaging system, a patient mounted pneumatic headset system;

an error microphone connected to said patient mounted pneumatic headset measuring an acoustic noise signal at an ear of said patient; and a noise cancellation processor producing an acoustic noise signal canceling waveform, said acoustic noise signal canceling waveform being a delayed and inverted acoustic noise signal output from said error microphone.

DETAILED DESCRIPTION

Figure 1:
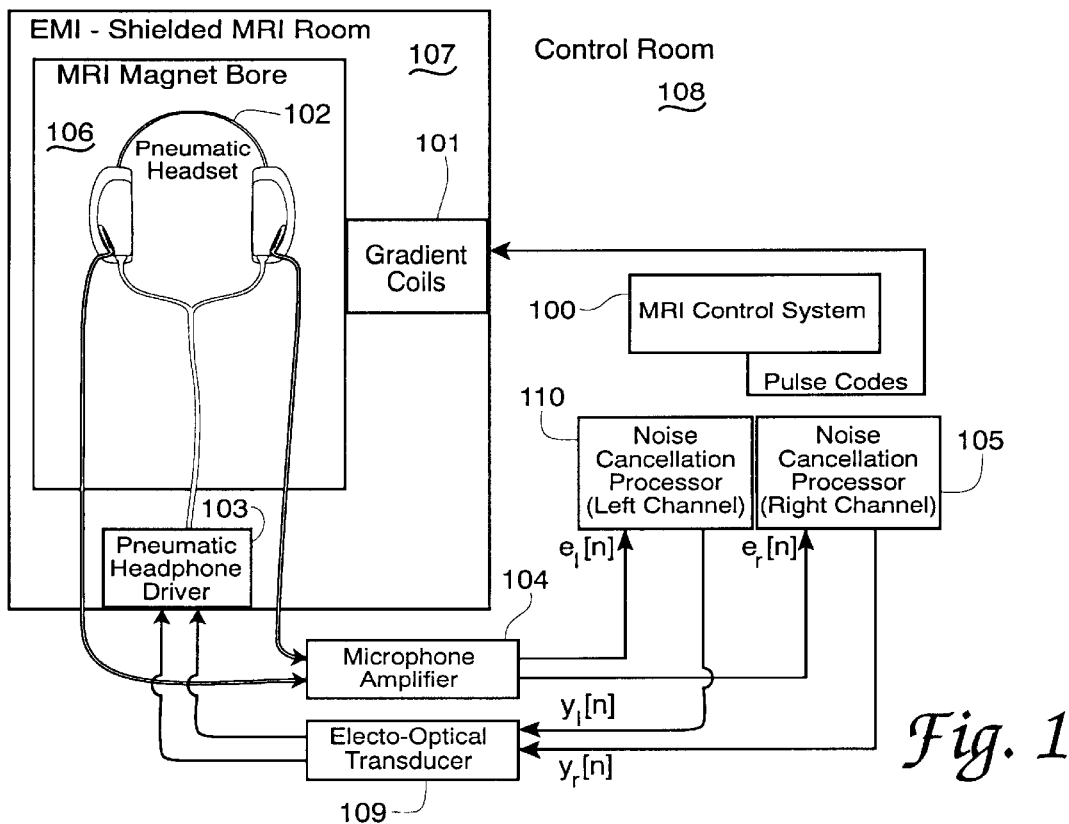
FIG. 1 shows a schematic diagram of the magnetic resonance imaging noise cancellation system of the invention.

The delay based active noise cancellation system for magnetic resonance imaging of the invention represents a novel way of canceling noise that has been tailored to meet the needs of noise cancellation in a MRI system and has substantial advantages over previous noise cancellation systems used with MRI. An overall diagram of the MRI noise cancellation system is shown in FIG. 1. The MRI noise cancellation system can be divided into four major subsystems, the MRI system, shown at 100 and 101 in FIG. 1, the pneumatic headset system shown at 102 and 103, the error microphone, shown at 104 and the noise cancellation processor shown at 105.

The subsystems and components of the system of FIG. 1 are divided by location into three areas representing different levels of shielding from the magnetic field of the MRI. The innermost level, represented at 106, is the magnetic bore of the superconducting MRI magnet. In this region, both the static magnetic field from the superconducting magnet (up to 3.0 Telsa) and the electromagnetic fields caused by the gradient coils of the MRI are largest. It is generally not acceptable to have any type of ferromagnetic material inside the magnet bore due to the strong magnetic fields in this region, and any type of non-ferrous conducting material will impede the operation of the MRI system. Therefore, all objects within this region should be plastic, glass, or some other non-metallic material.

The second region, represented at 107 in FIG. 1, is the EMI-Shielded MRI room, where the actual MRI system is located. This room is surrounded by conducting material to protect the surrounding environment from the substantial electromagnetic interference caused by the RF- and gradient-current pulses used during MRI. Because of the orientation of the magnets used for the MRI, the magnetic field strengths are substantially lower in this region than inside the magnet bore. However, the use of ferromagnetic materials in this room should be avoided as these magnetic fields can still be quite strong. Furthermore, any electronic devices or conductive cabling located in this room will be exposed to substantial electromagnetic interference (EMI). Therefore, it is necessary to avoid the use of metallic conductors and electronic devices in this room as much as possible.

The outermost room, represented at 108 in FIG. 1, is the Control Room, where the MRI control computers are located. This room is shielded from the EMI caused by the MRI, so the electronics needed to run the MRI system are located in this room.

MRI System

The MRI system, represented at 100 in FIG. 1, is a standard magnetic resonance imaging system of the type currently in widespread use for medical imaging. MRI systems are able to identify different types of tissue within the human body by placing the tissue in a strong magnetic field generated by a superconducting magnet and exciting the tissue (specifically the spin states of the molecules within the tissue) with a pulse of RF energy, and then measuring the electromagnetic emissions of the tissue as its spin states relax to the rest position. The MRI scanner is able to map the spatial locations of the different types of tissue by creating gradients in the magnetic field that change the response of the tissue as a function of spatial location within the body. The noise created by the MRI is believed to result from "knocking" of the gradient coils and RF coils against their mountings as current is pulsed on and off in the coils.

The proposed noise cancellation system operates independently of the MRI system, and requires no direct connection to the MRI.

Pneumatic Headset

Due to the restriction against the use of conducting or ferromagnetic materials inside the magnet bore, it is impossible to use traditional electro-dynamic headphones to generate a signal at the ears of a patient inside the MRI. However, it is very useful for the MRI operators to be able to communicate with the patient during the scan in order to provide verbal instructions. Furthermore, it is now standard practice to play music for the patient during the scan to reduce patient anxiety and make the scanning process more tolerable. Therefore the patient in the MRI is generally provided with a pair of pneumatically-driven headphones of the type once used on commercial aircraft. Pneumatic headphone systems specifically designed for use in the MRI are now commercially available. The present invention uses pneumatic headphones in combination with an ear-muff type hearing protector.

Figure 2A:
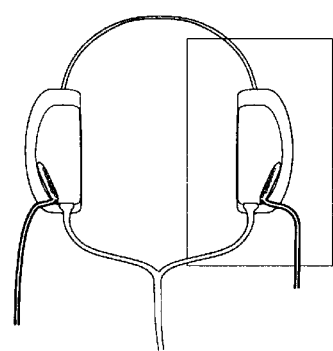
FIG. 2 shows a detailed view of the pneumatic headset of the FIG. 1 noise cancellation system.
Figure 2B:
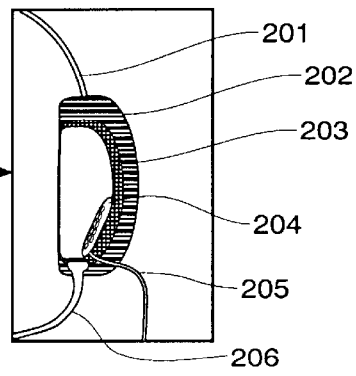

FIG. 2a shows a detailed description of pneumatic headphones according to the invention, and FIG. 2b shows a blown-up view of a single headphone. The entire head set is shown at 200 in FIG. 2a. A blown up view of the headset is shown in FIG. 2b with the headband shown at 201, a rigid ear cup shown at 202, and soft foam or gel ear seals, filled with sound absorbent material shown at 203. A microphone is shown at 204 with a microphone cable shown at 205 and plastic tubes approximately 3 m in length are shown at 206 and pass outside the magnet bore to a shielded pneumatic headphone driver unit inside the EMI shielded room which generates the acoustic signals propagated down the tubes. Referring again to FIG. 1, in order to reduce electromagnetic interference with the audio signals, the desired audio signals are passed into the EMI room, 107 in FIG. 1, via a fiber-optic transmission system from an electro-optical transducer shown at 109 located in the control room 108. The desired audio signals are sent to transducer 109 from the two channels of the noise cancellation system, shown at 105 and 110.

Error Microphones

Effective cancellation of the noise inside the MRI system requires some means of measuring the noise occurring at the ears of the patient. This is achieved by mounting a non-magnetic transducer inside the headphones near the opening of the pneumatic tubes carrying the headphone signal to the headset. Types of transducers for measuring acoustic noise inside the magnetic bore of the MRI include non-magnetic microphones, including capacitance-type, and microphones as well as piezo-electric or electret microphones which are capable of directly measuring sound fields inside the magnetic bore and can be placed directly inside ear-cup. These types of transducers offer minimum propagation delay and optimal frequency response, but, because they are metallic and require a conductive cable to carry the sound signals outside the magnet bore, they are both susceptible to electromagnetic interference due to the MRI scan and prone to introduce undesired artifacts into the MRI image. A preferred class of transducers use pneumatic tubing to carry the sound signal inside the earcup outside the magnetic bore, where the tubes are attached to electret-type microphones that record the acoustic signal. This method of measuring acoustic noise inside the earcup does not require any metallic materials inside the magnet bore, but introduces a substantial acoustic propagation delay (several milliseconds) as the sound travels down the tubes to the microphones. The noise cancellation algorithm used in the present invention is relatively robust to propagation delays, so either type of microphone could be used effectively in this system.

Noise Cancellation Processor

Figure 3:
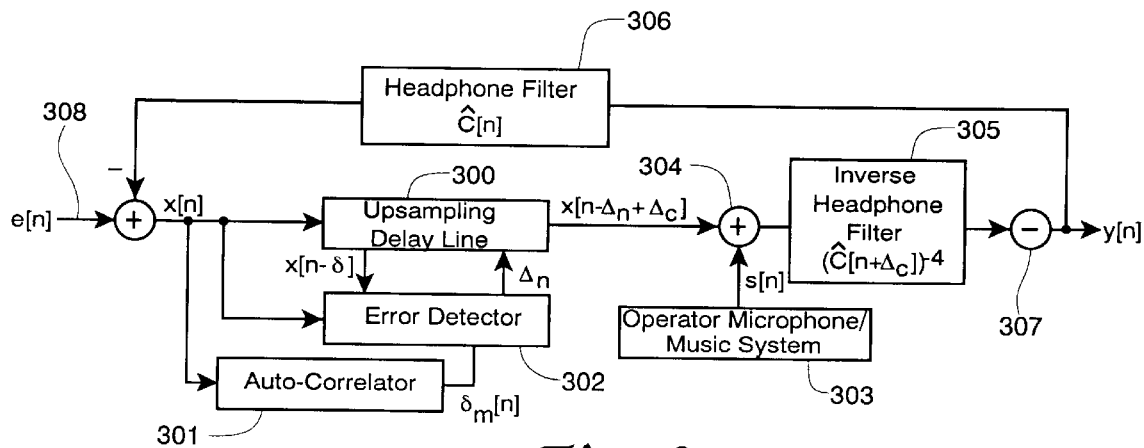
FIG. 3 shows a diagram of a noise cancellation processor according to the invention.

The noise cancellation processor of the invention uses an adaptive delay algorithm to produce a delayed and inverted version of the noise signal that cancels the MRI noise near the patient's ears. Note that the noise cancellation processor is identical for the left and right ears, so only one implementation is described here. The cancellation processor is shown in FIG. 3 of the drawings. The cancellation processor of FIG. 3 includes an upsampling delay line at 300, an auto-correlator at 301, an error detector at 302, an operator microphone/music system at 303, an adder at 304, an inverse headphone filter at 305 and a headphone filter at 306. The input signal enters the processor at 308 and exits the processor at 307.

Considering the method and device of the invention operationally, first, the output signal generated by the system at the location of the error microphone ($y[n] * \hat{C}[n]$) is subtracted from the raw error signal $e[n]$, represented at 308 in FIG. 3, measured at the microphones inside the headset to isolate the MRI noise signal $x[n]$ from the error signal. The noise signal $x[n]$ is fed into the auto-correlator at 301 that selects the three sample delays $\delta_m[n]$ that are most likely to reflect the repetition rate of the MRI noise signal. Then an error detector 302 compares the signals $x[n-\delta_m]$ and $x[n]$ to determine which delay value $\Delta_n$ results in the smallest residual noise signal $x[n] - x[n-\Delta_n]$. The resulting delay value is fed into an upsampling delay line at 300 that delays the signal by $\Delta_{n-\Delta_c}$ samples where $\Delta_c$ is the propagation delay of the transmission path from the headphone transducers to the error microphone. The desired auditory signal $s[n]$, which can include either operator instructions recorded at a microphone in the control room or music originating from a sound system in the control room, represented at 303, is added to the output of the delay line before the signal is processed with an inverse headphone filter ($\hat{C}[n+\ddot{A}_{cD}]^{-1}$, shown at 305, that corrects for the spectral characteristics of the headphone transducers and the propagation path to the error microphones. The output signal is then inverted and the resulting signal $y[n]$ is output to the headphone transducer to produce the noise cancellation signal at the ears of the patient. Finally, the output signal $y[n]$ is convolved with the headphone filter $\ddot{C}[n]$ at 306 approximating the propagation path from the headphone transducers to the error microphone and subtracted from the error signal $e[n]$ measured at the microphone in order to approximate the raw input signal $x[n]$ representing the uncancelled acoustic noise waveform of the MRI system.

Figure 4:
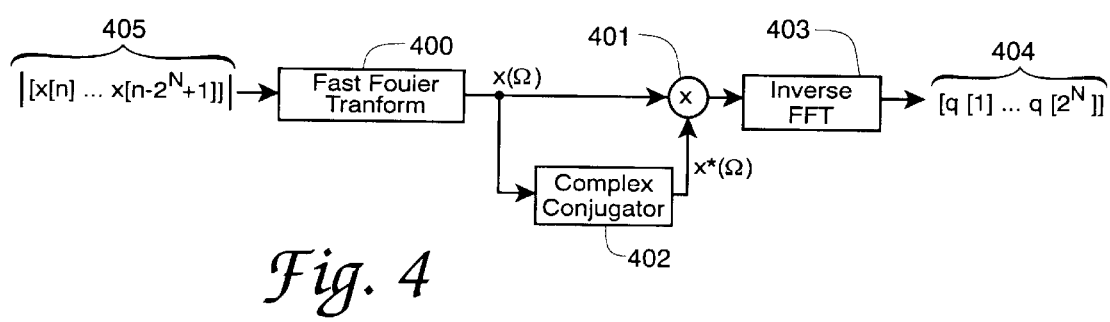
FIG. 4 shows an auto-correlator of the noise cancellation processor of FIG. 3.
Figure 5:
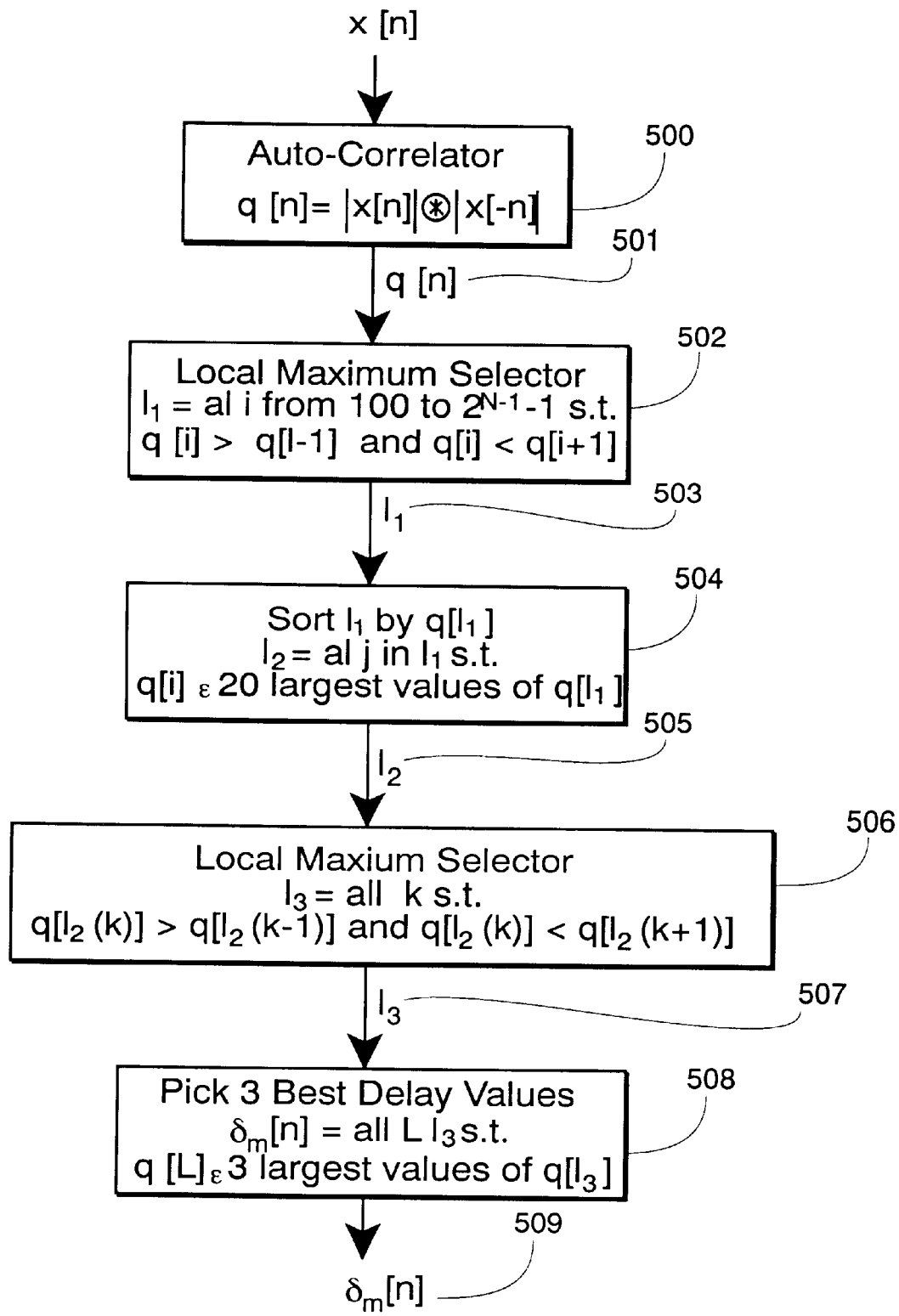
FIG. 5 shows a flow graph of the delay selection algorithm according to the invention.
Figure 6:
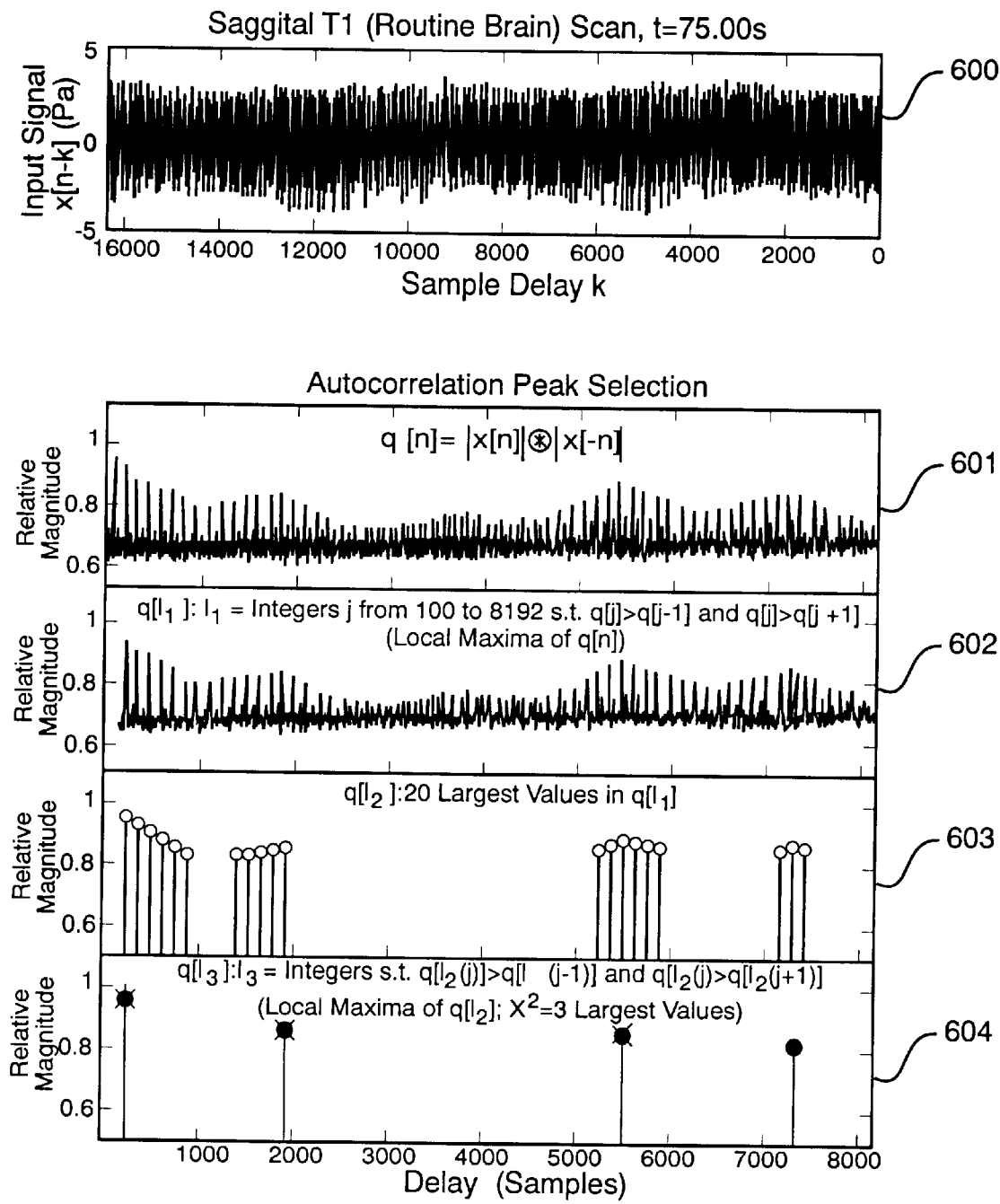
FIG. 6 shows examples of each step of the delay selection algorithm of FIG. 5 of a routine brain scan.

The outer layer of the delay-based MRI noise cancellation system of the invention is a noise signal autocorrelator that determines the approximate repetition rate of the MRI noise signal. A diagram of such an autocorrelator is shown in FIG. 4. The autocorrelation system examines the periodicity of previous $2^N$ samples of the net MRI noise signal at the ears, and chooses up to three signal delays that have the greatest likelihood of substantially reducing the total noise signal at the patient's ears. A flow graph of the delay selection algorithm is shown in FIG. 5. FIG. 6 shows the output of each stage of the algorithm for a typical MRI noise signal. Note in FIG. 6 that N=14, so the previous 16384 samples of the input signal are used in the autocorrelation.

The function of the auto-correlator and delay selection algorithm is best illustrated by considering a series of stages. The first stage of the autocorrelator system is the actual autocorrelator, shown in FIG. 4. The autocorrelator of FIG. 4 operates in three stages. First, it takes the Fast Fourier Transform (FFT) of the absolute value of the previous $2^N$ samples of the input signal $x[n]$, represented in block 400 of FIG. 4. It then multiplies the resulting Discrete Fourier Transform (DFT) coefficients $X(\Omega)$ by their complex conjugate $X(\Omega)^*$ (which is equivalent to taking the circular convolution of the signals $x[n]$ and $x[-n]$ in the time domain), the multiplier represented at 401 in FIG. 4 and the complex conjugator represented at 402. Finally, the autocorrelator takes the inverse FFT, represented at 403 in FIG. 4, of the resulting DFT coefficients to generate the absolute autocorrelation signal $q[n]$, represented at 404 in FIG. 4. Note that, since the DFT coefficients $X(\Omega) \cdot X(\Omega)^*$ must be real and even, the resulting autocorrelation signal $q[n]$ is also real and even and is symmetric about the point $n=2^{N-1}$. Also note that, since the autocorrelator is essentially equivalent to circular convolution in the time domain, the signal $q[n]$ is effectively aliased. Also, taking the absolute value of $x[n]$ prior to the autocorrelation, represented at 405 in FIG. 4, enhances the peaks in the autocorrelation function in the vicinity of the optimal delay values.

The second stage of the autocorrelator system is illustrated in the flow graph of FIG. 5 at 501–509, with the first stage represented at 500. The second stage selects the indexes I, corresponding to the local maxima of the signal $q[n]$ for n>100, shown at 501 in FIG. 5. AR of the delays that are capable of canceling the signal are multiples of the fundamental repetition rate of the MRI scan, so only the peak values of $q[n]$ are of interest. Although this stage appears to have only a minimal effect on $q[n]$, in fact it limits the signal in the vicinity of each peak in $q[n]$ to a single sample. Thus the output of this stage has only a single large value of $q[n]$, shown at 501, at each multiple of the fundamental period. Note that the indexes are limited to those greater than 100 to allow some slack in the desired delay time for the delays associated with the inverse headphone filter and the propagation path from the headphones to the error microphones.

The third stage of the autocorrelator system, represented at 504 in FIG. 5, sorts the indexes $I_1$, represented at 503, decreasing order by the magnitude of the correlation function $q[I_1]$ and then selects the 20 indexes $I_2$, represented at 505, corresponding to the largest values of $q[I_1]$. This highlights only the most prominent peaks in the autocorrelation signal.

The fourth stage of the autocorrelator system, shown at 506 in FIG. 5, selects the indexes $I_3$, represented at 507, corresponding to the local maxima of the signal $q[I_2]$. These points effectively correspond to the local maximums of the envelope of the autocorrelation signal.

The final stage of the autocorrelator system, shown at 508 in FIG. 5, assigns the indexes of the three largest values of $q[I_3]$ to the three output delays $\delta_m[n]$, represented at 509. These three delays correspond to the delays A most likely to minimize the residual noise signal $x[n]-x[n-\Delta_n]$.

FIG. 6 shows examples of each step of the delay selection algorithm of FIG. 5 on a routine brain scan. The top panel 600 of FIG. 6 shows the input signal. Panel 601 shows the auto-correlation signal for a typical MRI scan. Panel 602 illustrates that the signal is unique for only 2N-1 (8192) samples. The most striking feature of the auto-correlator signal is the appearance of sharp spikes at regular intervals, shown at 603. These spikes represent the fundamental period of repetition in the MRI scan. Panel 604 shows the local mean.

Upsampling Delay Line

Referring again to FIG. 3, the second major component of the noise cancellation processor of the invention is an upsampling delay line that allows retrieval of the previous $2^{N-1}$ samples of the reference signal x[n] with a variable delay having $\frac{1}{10}^{th}$ of sample resolution. The upsampling delay line is shown at 300 in FIG. 3 as a single component of the entire noise cancellation processor. Although there are many possible ways to implement this system, the present arrangement simply upsamples the signal by a factor of ten, convolves the upsampled signal with a reconstruction filter using sparse convolution, and stores the previous $10*2^{N-1}$ samples of the upsampled signal in a circular buffer. The sample with delay $\delta$ (i.e. the value x[n-$\delta$] can be retrieved directly by choosing the proper index of the circular buffer. In this particular implementation, the delay is represented as a floating point number in terms of the number of samples of delay in the original signal x[n]. Note that the delay line has two purposes: allowing the error detector subsystem to evaluate different delay values and select the optimum delay value for cancellation, and delaying the reference signal by this optimum delay for output as the cancellation signal.

The code for the delay line in C++ is shown in the Appendix. The code represents the upsampling delay line as a class called circbuffer. The class includes methods for adding a sample to the buffer (addsample(int sample)), and for retrieving the sample with a given delay (value(float delay)). A 201 point reconstruction filter (low pass filter) determined by MATLAB is used to interpolate the upsampled signal. Since the upsampled signal is zero at 9 out of every 10 samples, sparse convolution can be used for the reconstruction filter (i.e. each delay from 0 to 0.9 samples can be computed by multiplying and adding only 21 of the 201 coefficients of the reconstruction filter with the last 21 values of the input signal.) Thus fewer than 210 multiplies for each sample of the original signal are needed to generate all 10 corresponding samples of the upsampled signal.

Error Detector

In the FIG. 3 drawing, the error detector subsystem, the third major subsystem of the noise cancellation processor, is shown at 302. The error detector subsystem is responsible for evaluating the three possible delay values $\delta m$ selected by the auto-correlator and choosing the delay value that will provide the best attenuation at the patient's ears. The error detector also adjusts the crude integer-valued delays provided by the auto-correlator to find partial sample delay (to within 0.1 samples) that maximizes performance, and turns the cancellation signal off when the cancellation signal is no longer effectively reducing the noise. The basis of the error detector is an error metric that determines the energy in the error signal over the previous 128 samples:

$$\varepsilon(n,\delta) = \sum_{k=0}^{127} (x[n-k] - x[n-k-\delta])^2 \quad (1)$$

where n is the current sample number and $\delta$ is the desired delay (note that since we are using the upsampling delay line we allow the delays $\delta$ to be expressed as a decimal in tenths of samples). During each iteration, the error detector calculates seven error values $$\varepsilon_o = \text{Raw (uncanceled) signal power} = \sum_{k=0}^{127} (x[n-k])^2$$

$\epsilon_c$=Error with current delay value=$\epsilon$(n, $\Delta_{n-1}$)

$\epsilon_{c+}$=Error with current delay value+0.1 sample=$\epsilon$(n, $\Delta_{n-1}$+0.1)

$\epsilon_{c-}$=Error with current delay value+0.1 sample=$\epsilon$(n, $\Delta_{n-1}$+0.1)

$\epsilon_{\delta 1}$=Error with first delay suggested by autocorrelator=$\epsilon$(n, $\delta_1$[n]+r)

$\epsilon_{\delta 2}$=Error with second delay suggested by autocorrelator=$\epsilon$(n, $\delta_2$[n]+r)

$\epsilon_{\delta 3}$=Error with third delay suggested by autocorrelator=$\epsilon$(n, $\delta_3$[n]+r)

Note that $\Delta_{n-1}$ is the delay value output by the system in the previous interaction (the "current" delay value) and r is a random variable from−0.5 to 0.5 that "dithers" the integer-valued delays suggested by the autocorrelator to ensure that the best partial sample delay is chosen. Without the dither, the selection would always be based on the best integer delay even if the error were significantly smaller for a different delay shifted by a partial sample.

In order to prevent spurious changes in the delay value, the error detector is biased in favor of maintaining the current delay value in two ways. First, the delay value will not be changed unless there is significant energy in either the raw signal $\epsilon_o$ or the canceled signal with the current delay $\epsilon_c$. In the present implementation, the cutoff value for these errors is 10 pascal$^2$. Second, the delay value will not be changed by more than a tenth of a sample unless the new delay produces at least an 80% decrease in the energy of the error signal. Finally, if the best delay available generates an error signal with more than 5 times the energy of the raw $\epsilon$ (uncanceled) signal, the delay is set to−1 and the output of the upsampling delay line is turned off entirely (set to zeros). The ability to turn off the cancellation signal prevents the system from inadvertently increasing the noise signal under adverse circumstances. The logical statement of the selection is provided in the appendix.

Figure 7:
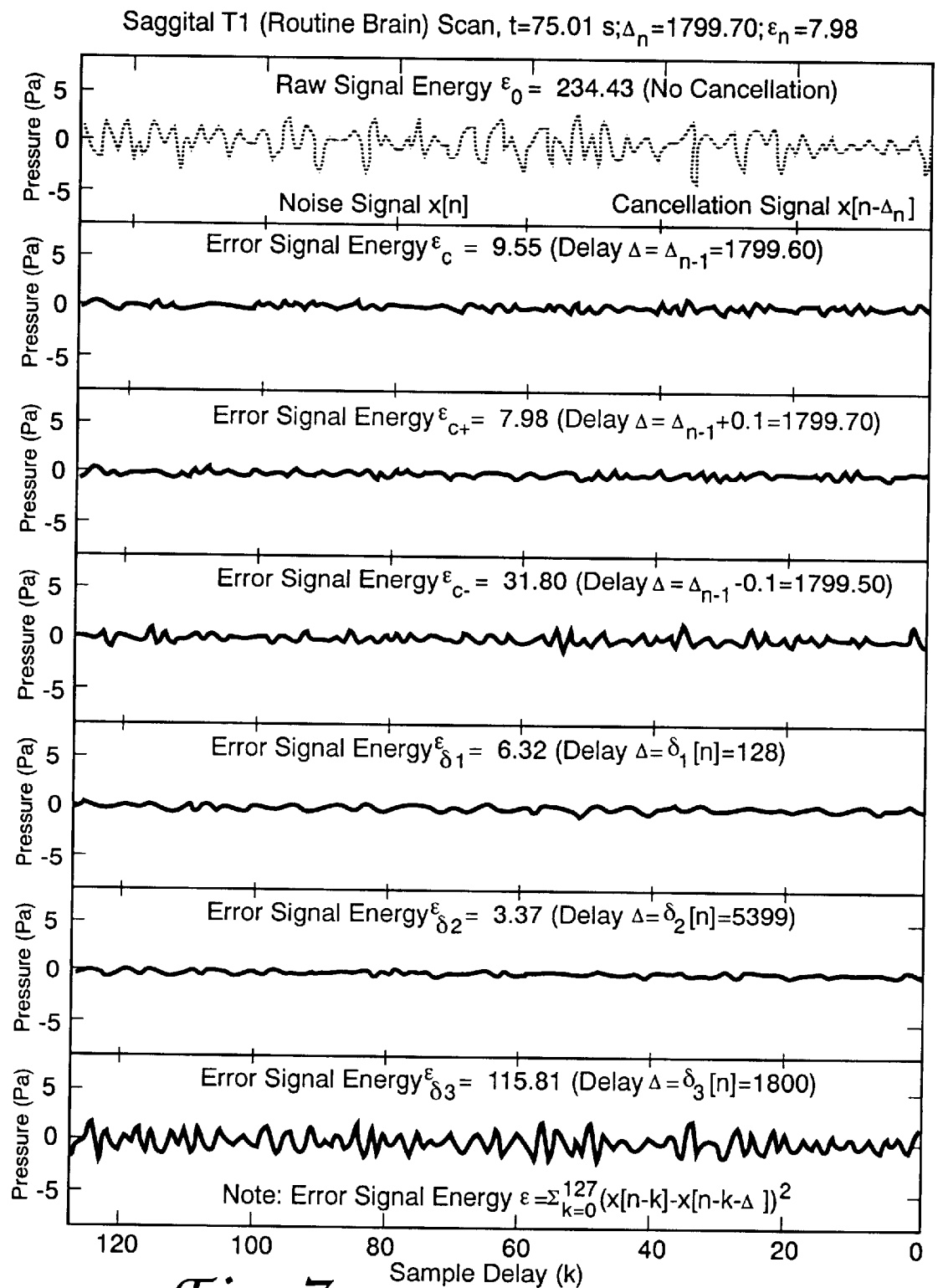
FIG. 7 shows a graph illustrating the operation of the delay selection algorithm on a typical MRI noise waveform.

The operation of the error detection system on a typical MRI acoustic noise waveform, the same one operated on in the flow graph of FIG. 5 is depicted in FIG. 7. The top panel 700 shows the noise waveform x[n] and the cancellation signal x[n-$\Delta_n$]. Note that the two signals almost exactly overlay one another. In this example, the error $\epsilon_{c+}$(7.98) for the current delay plus 0.1 samples (1799.7 samples) is smaller than the error $\epsilon_c$ (9.55) with the current delay $\Delta_{n-1}$ of 1799.6 samples. Therefore, the system selects the new delay $\Delta_n$ to be 1799.7 samples. Also, note that both the errors with delays $\delta_1$[n] (128 samples) and $\delta_{2[n]}$ (5399 samples) are smaller than the error of the selected delay $\Delta_n$, but that neither meets the criteria of being 80% smaller than the error with the previous delay $\Delta_{n-1}$. In this case, the delay value selected reduces the energy in the error signal 96.6 % (14.7 dB). Note that, while the selected delay did not minimize the error in this case, the criterion limiting changes in the current delay improves the stability of the system and generates better performance over the entire waveform.

Note that the delay implemented by the upsampling delay line is not $\Delta_n$ but rather $\Delta_n$-$\Delta_c$, where $\Delta_c$ represents the propagation delay of the headphone transduction system. By subtracting this propagation delay from the delay of the incoming signal, it is possible to make the inverse headphone filter, 305 in FIG. 3, a causal filter. The only restriction on $\Delta_c$ is that it must be less than 100 samples, which is equivalent to the smallest delay the autocorrelation system will select.

Music Signal/Control Room Microphone

During the MRI process it is often necessary to give verbal instructions to the patient from a microphone located in the MRI control room. Furthermore, to reduce patient anxiety and help mask the acoustic MRI noise, it is desirable to provide the patient with music during the MRI scan. In current MRI scanners, both functions are fulfilled with a standard set of pneumatic headphones producing a speech/music signal at the ears of the patient. In the proposed system, the speech/music signal must be produced at the patient's ears at the same time as the noise cancellation signal without interfering with the noise cancellation process. An operator/microphone music system, shown at 303 in FIG. 3 is, therefore, an option for use in the noise cancellation processor of the invention. This can be accomplished by adding the speech/music signal directly to the noise cancellation signal. Since the noise cancellation signal is electronically subtracted from the signal received at the error microphones near the patient's ears to generate the raw reference signal x[n], the speech/music signal will also be eliminated from the reference signal and will not interfere with the noise cancellation signal.

Inverse Headphone Filter

At this stage in the algorithm, the error detector has selected the signal $x[n-\Delta_n]$ that will cancel the incoming noise signal. However, the headphone transduction process will transform this cancellation signal before it reaches the patients ears into a signal that no longer cancels the input signal. Therefore it is necessary to introduce an inverse headphone filter that corrects for the frequency response of the headphones and produces an acoustic signal $x[n-\Delta_n]$ at the patient's ears that will cancel the MRI noise signal. This major component of the noise cancellation processor is shown at 305 in FIG. 3. In fact, the inverse filter should account for the entire transmission loop from input of the headphone system to the resulting electrical input recorded at the error microphones inside the headphones. Since the microphones are located at fixed points near the sound source inside the headphones, as shown at 204 in FIG. 2, this transfer function should be relatively stable. Furthermore, since the microphone is included in the loop, the transfer function can be measured directly using either a frequency analyzer or a time-domain system identification system such as a golay code analysis. The resulting impulse response, $\hat{C}[n]$, can be time advanced by $\Delta_c$ samples in order to eliminate the propagation delay and make the inverse filter causal. Then an inverse filter can be found using fourier transform techniques.

The output of the Inverse Headphone Filter is inverted, represented at 307 in FIG. 3, to form the waveform cancellation signal y[n] that is sent directly to the headphone driver system. The resulting acoustical signal will cancel the acoustic MRI noise at the patient's ears.

Headphone Filter

The noise cancellation system requires access to the raw (uncanceled) acoustic noise signal present at the ears of the patient in order to delay that signal to form the noise cancellation waveform. However, the signal measured at the locations of the error microphones is the sum of the raw signal and the cancellation signal. In order to reconstruct the raw signal, it is necessary to subtract the cancellation signal from the canceled signal e[n] measured by the microphones. This is accomplished by convolving the output signal y[n] with the impulse response $\hat{C}[n]$ of the headphone driver to error microphone propagation loop described in the previous section, and subtracting the resulting signal (which is equivalent to the electrical signal from the microphone produced by the acoustic cancellation signal) from the input of the error microphones. The resulting signal, x[n], is the desired raw (uncanceled) MRI noise waveform.

Although parts of this algorithm are computationally intensive, the relatively slow sample rate (4 kHz in this implementation) makes it a manageable burden for most current DSP processors. Furthermore, it is not necessary for all parts of the algorithm to execute every sample. In this system, the real-time autocorrelator operates only once every 128 samples, and the error-detector system operates once every 32 samples. Only the upsampling delay line, inverse headphone filter, and headphone filter stages must execute every sample. One way of implementing this system on a single processor is divide the processing between an interrupt-driven inner function that executes every sample, and a free-running outer function that performs the auto-correlation. On each sample interval, an interrupt would activate the delay-line, inverse headphone filter, and headphone filter processing and perhaps the calculation of one of the error signal energy values in the error detector. The outer loop, which would perform the real-time auto-correlation, would use the remaining cycles of the processor between samples.

FIGS. 8a–8d shows the simulated performance of the system for four different scans measured on a General Electric Signal 1.5 Telsa Horizon LX Magnetic Resonance Scanner with a fiber-optic microphone system. The top panel of each scan, 800, 801, 802 and 803 shows the original waveform x[n] in dark gray, and the simulated noise-canceled waveform x[n]+y[n] in light gray. The second panel for each scan, 804, 805, 806 and 807 shows the delay value $\Delta_n$ selected to minimize the power of the noise-canceled signal. The third panel of each scan, 808, 809, 810 and 811 shows the A-weighted noise level of the pre- and post-canceled scan, measured with an exponential-decay time window with time constant $\tau$=0.125 s. The last panel of each scan, 812, 813, 814 and 815 shows the attenuation performance of the cancellation system, which is the decibel level of the pre-canceled MRI noise minus the decibel level of the post-canceled noise. The last panel of each scan also gives some summary statistics of the noise-cancellation performance. The first statistic is the average attenuation over the region where the raw MRI noise exceeds 80 decibel SPL. This metric measures noise cancellation performance only in the region where there is significant acoustic MRI noise. The second metric is the percentage of time the output signal is greater than 90 decibel SPL, which measures the proportion of the time when noise-exposure to the patient is highest (and most irritating) both before and after the cancellation.

Note that a common feature of all scans in the Signa scanner, FIGS. 8a–8d, is an initial prescan signal consisting of six closely spaced (approximately 40 ms spacing) clicks, several longer-spaced (approximately 2 s spacing) clicks, and three loud noise bursts exceeding 100 decibel SPL output for approximately 15 seconds. The noise cancellation system does an adequate job of canceling the impulsive clicks that start the pre-scan process, canceling several of the closely-spaced clicks and the last few longer-spaced clicks. It performs extremely well on the loud noise bursts in the pre-scan, canceling the overall noise by 20 dB or more over the vast majority of the noise bursts (excepting short onset and offset noises at the beginning and end of each noise burst.

Figure 8A:
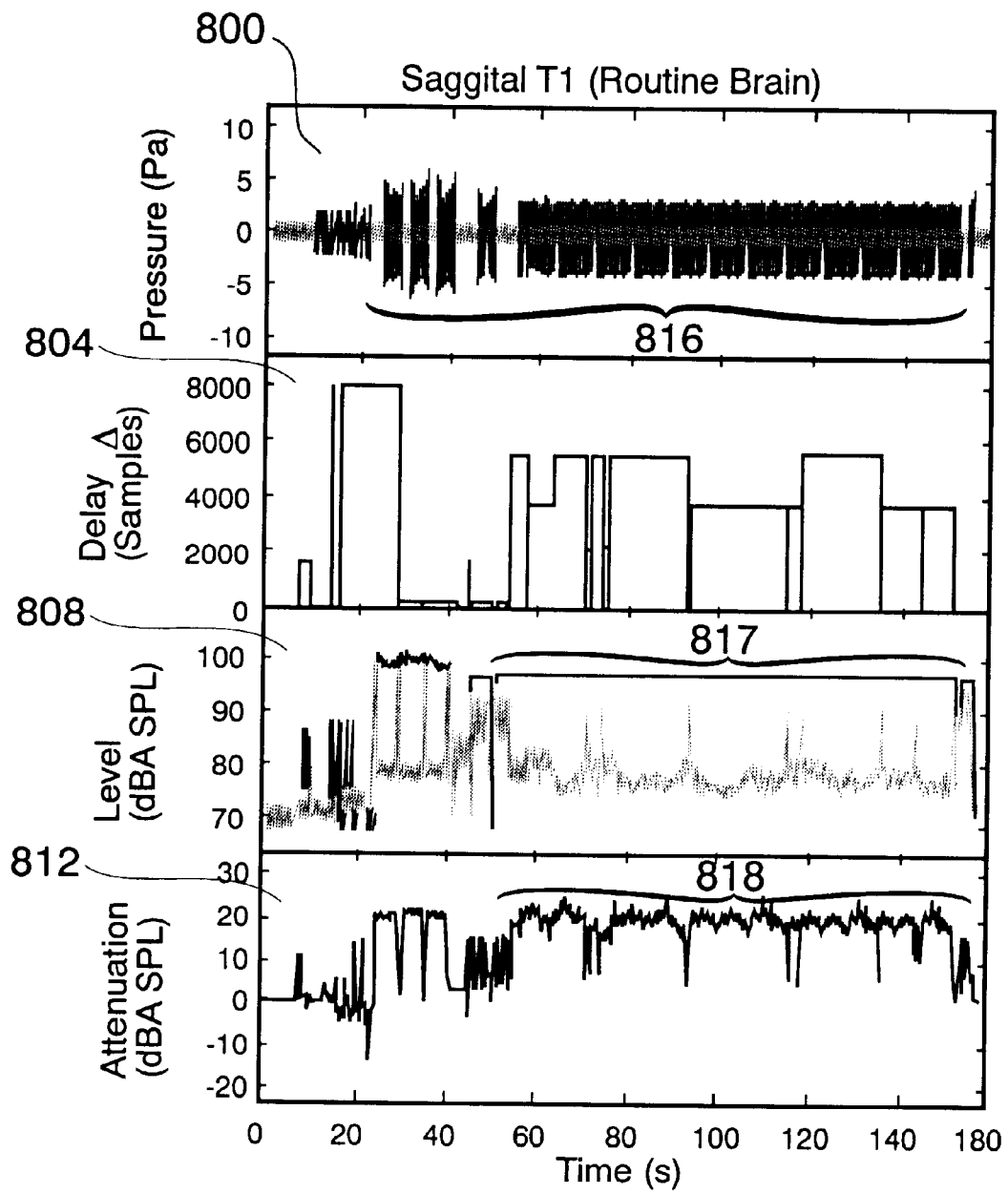
FIG. 8 shows a graph illustrating the performance of the noise canceling system of the invention.

The FIG. 8a T1 Routine brain scan, a routine brain scan, is an example of the type of scan generating the best performance in the noise-cancellation system. The main portion of the scan (from about 40 s on) shown at 816, produces a continuous, high-output noise producing approximately 98 dBA SPL for almost 2 minutes. Initially, the noise-canceling algorithm generates about 10 dB of average attenuation by using a short delay of 3.2 ms.

However, once the main portion of the scan begins, the system recognizes that a much longer delay of 90 ms or 135 ms, illustrated at 817, produces a more substantial attenuation, and locks on to this delay value. This results in attenuation of approximately 18 dB over most of the duration of the scan, illustrated at 818. Overall, the portions of the scan where the raw noise exceeds 80 dB are attenuated by an average of 16.9 dB, and the portion of the scan exceeding 90 dB SPL is reduced from 79% to less than 4%.

Figure 8B:
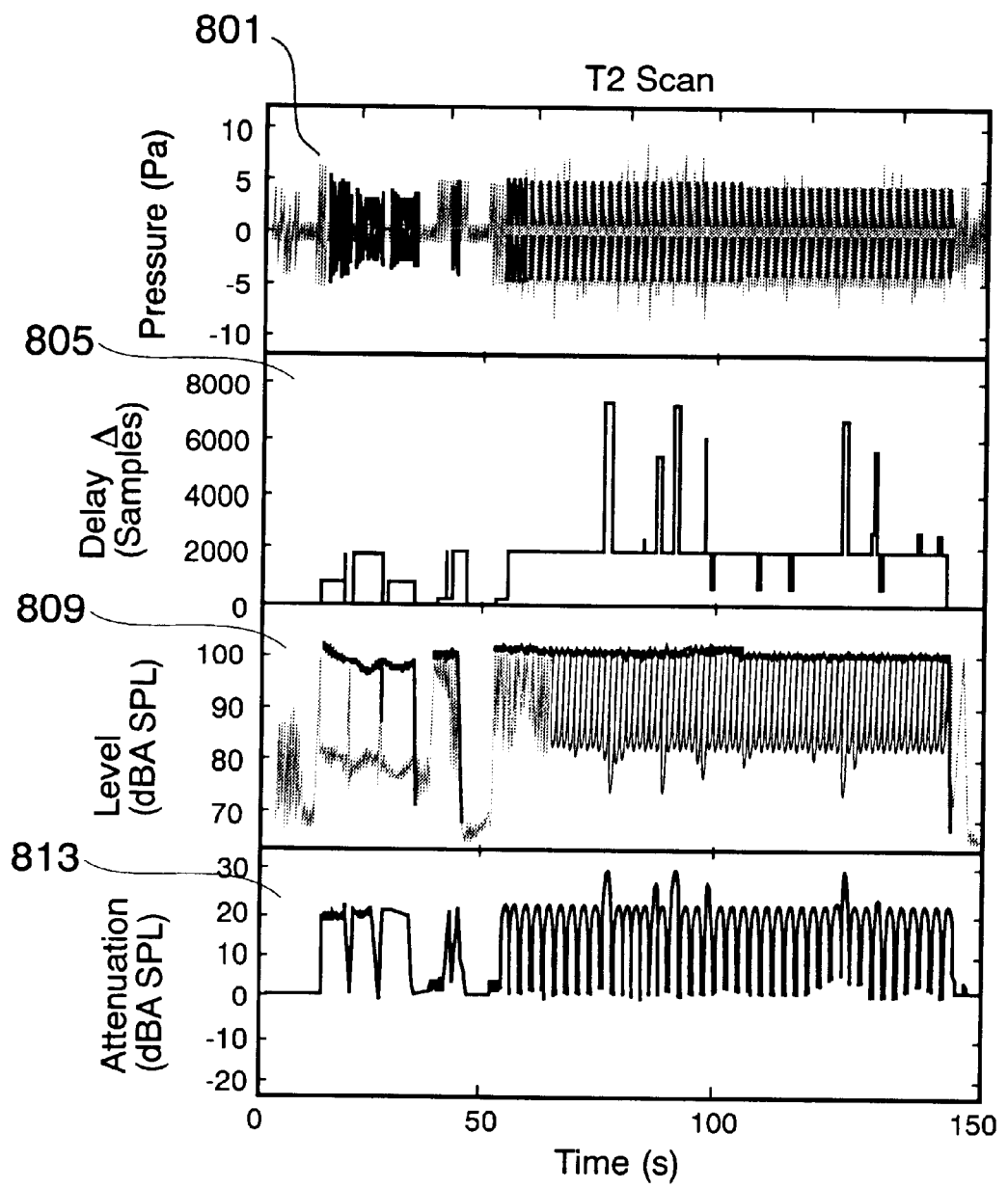
Figure 8C:
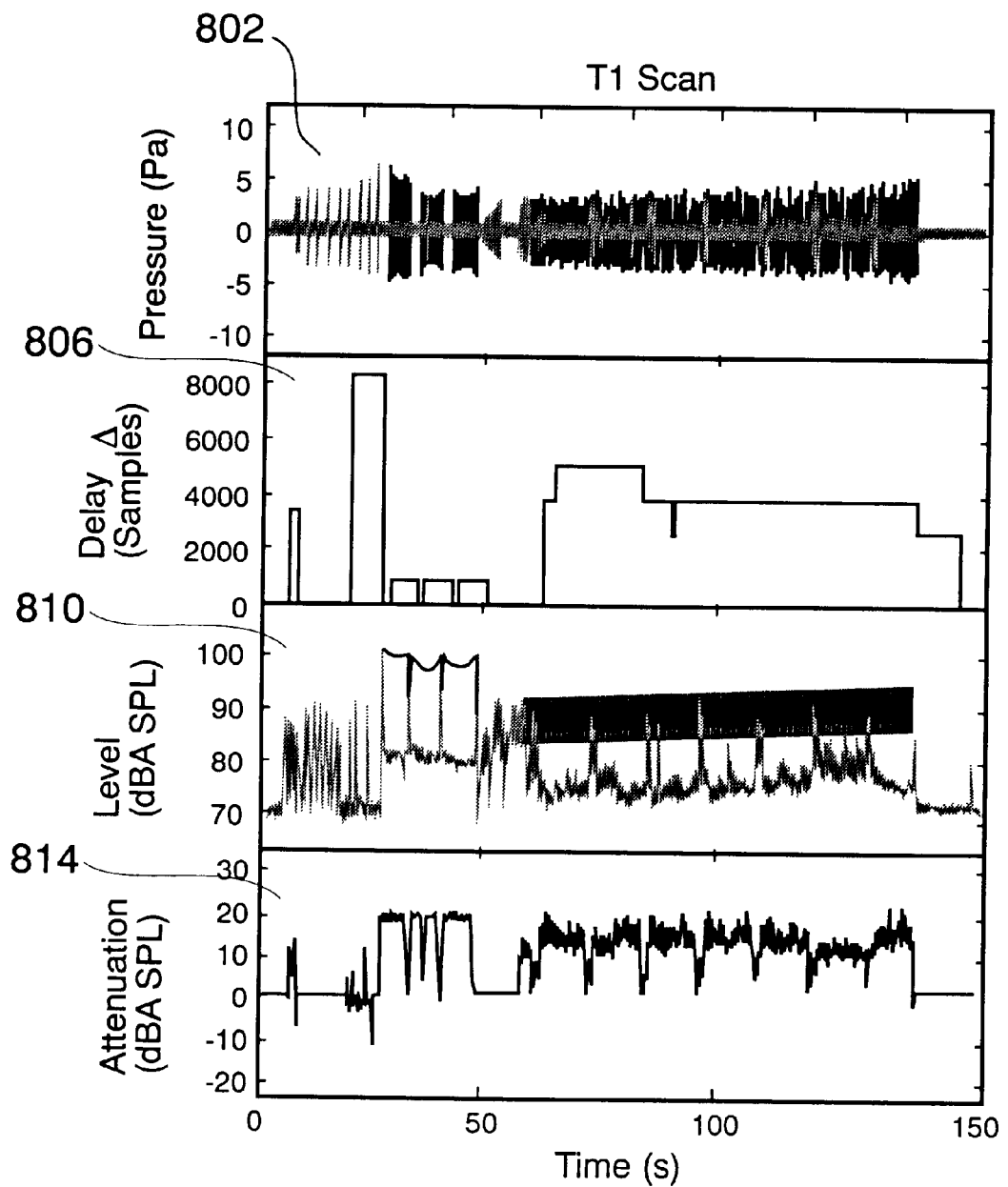

The FIGS. 8b and 8c scans represent scans where the performance of the system is still impressive but not as good as in the Routine Brain scan. In the FIG. 8c scan, the main portion of the acoustic MRI noise consists of repetitive impulse noises, similar to banging on the MRI machine with a hammer. Once the system locks onto this signal, it is able to cancel the impulsive noise by 15 dB or more, but at seven times during the scan the characteristics of the scan noise change and the attenuation is briefly reduced to about 5 dB. Overall, the system attenuates the loudest portions of this scan by 11.7 dB. In the FIG. 8b scan, the scan noise is a continuous, loud noise in excess of 100 dBA SPL. However, in this case the characteristics of the scan change substantially at regular intervals, and during these intervals the cancellation signal fails to cancel the acoustic noise. Consequently, the canceled waveform consists of loud noise bursts at regular intervals. Between these noise bursts, the acoustic noise is canceled by 20 dB. Although the noise-cancellation in this case is clearly not perfect, it still is substantial. Overall, the system cancels the loudest MRI noise by an average of 12.3 dB, and reduces the exposure of the patient to noise over 90 dB from 82% to 29%.

Figure 8D:
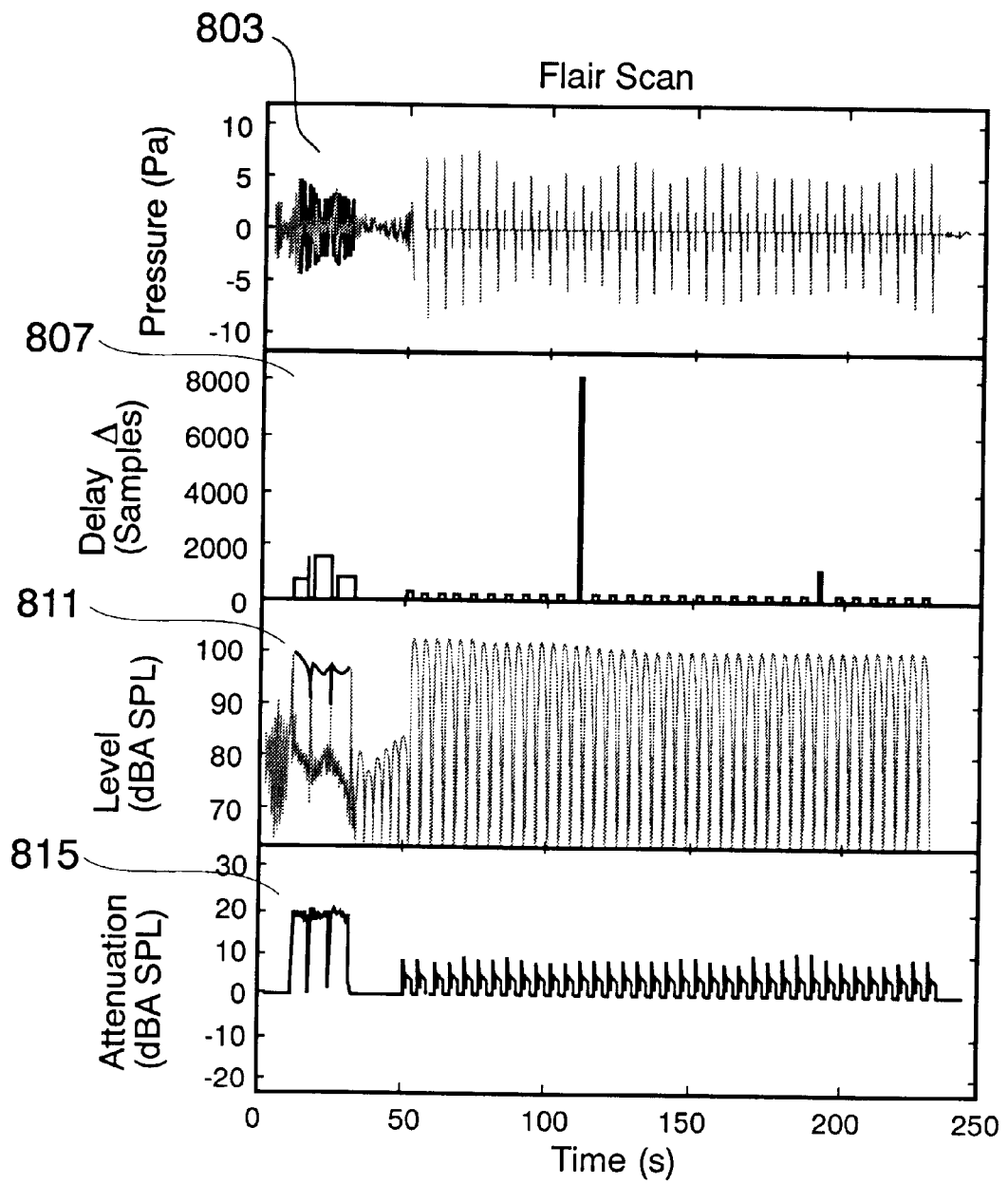

The FIG. 8d scan represents the worst-case behavior of the noise cancellation system of the invention. The main portion of this scan (which is nearly twice as long as the other two scans) consists of sets of five clicks and five loud noise bursts spaced at regular intervals of approximately five seconds. Although the system is able to lock in on a fundamental period of the noise bursts and cancel them by approximately 6 dB, the long periodicity of the signals exceeds the memory buffer used in the autocorrelation system (capable of handling periods up to 2 s) and therefore the system is not able to produce the 20 dB cancellations seen in the other scans. Nevertheless, the system still provides substantial attenuation to the scan, averaging more the 5 dB, and reduces the patient's exposure to sounds exceeding 90 dBA by 29% (from 29.6% to 21.1%).

Significant advantages of the MRI noise cancellation system of the invention include its ability to adapt instantaneously to changes in the characteristics of the MRI system. In traditional noise cancellation systems, using adaptive algorithms like the LMS algorithm, the system must adapt to changes in the characteristics of the noise signal iteratively. Thus, many samples are required before the system converges to the optimal configuration when the characteristics of the noise change, as they do frequently in the course of an MRI scan. In the proposed invention, however, the system is capable of almost immediately selecting the proper delay to allow maximum cancellation, or turning off the cancellation signal if it is no longer properly attenuating the noise signal. The only adaptation required is to adjust the partial sample delay to best attenuate the noise signal. Thus the system is capable of adapting more rapidly to changes in the noise signal than traditional noise-cancellation systems.

Another advantage is its inherent stability. One problem with an adaptive algorithm such as the LMS algorithm is that, if the system attempts to adapt too quickly to a noise signal, it can become unstable and generate a large output. The proposed algorithm does not have this problem, because it never changes the gain applied to the input signal. Furthermore, the algorithm automatically turns off the cancellation signal whenever it determines that the cancellation signal is actually increasing the noise level at the patient's ears. Therefore the proposed algorithm is relatively immune to instability problems.

Another advantage is its ability to cope with substantial propagation delays in the impulse responses of the headphones and microphones. In the filtered-X LMS algorithm, a modified LMS algorithm that allows convergence when there is a propagation delay between the system output and the error microphone, there is a clear loss in performance both in adaptation time and maximum attenuation related to the delay of the headphone input- microphone-output propagation loop. In the proposed algorithm, however, the only processing occurring on the input signal is a delay, and the algorithm never selects a delay less than 100 samples. As long as the delay of the propagation loop is less than 25 ms, it can be implemented simply by reducing the delay inserted into the input signal by the number of samples of delay in the headphone to microphone loop with no loss in performance.

Finally, the MRI noise cancellation system and method of the invention is advantageous because of its ability to reduce MRI noise without integration into the MRI system (modularity). One major advantage of this system is that it is basically just a modification of an existing pneumatic headphone system and thus it can be implemented inside an MRI system without any modifications to the MRI at all. This allows seamless integration into the installed base of MRI systems with minimal cost and effort.

While the apparatus and method herein described constitute a preferred embodiment of the invention, it is to be understood that the invention is not limited to this precise form of apparatus or method and that changes may be made therein without departing from the scope of the invention which is defined in the appended claims.

---

APPENDIX A

Matlab code for Auto-Correlation Subsystem
%Auto-correlate absolute input signal at time i
q=abs(crosscorr(abs([x((i-2^14+1):i)']),abs([x((i-2^14+1):i)'])));
%Find local maxima
I1=find(q(2:8191)>q(1:8190) & q(2:8191)>q(3:8192))+1;
%Sort indices and choose 20 greatest values of q[n]
[y,ind2]=sort(-q(ind));
I2=I1(ind2);
I2=I2(find(ind>100));
I2=I2(1:20);
%Sort back into order of increasing index
[y,ind2]=sort(I2);
I2=I2(ind2);
%Find local maxima of q[I3]
I3=[0 find(q(I2(2:19))>q(I2(1:18)) & q(I2(2:19))>q((I2(3:20))))]+1;
I3=I2(I3);
%Sort to find largest 3 q[I3]
[y,ind2]=sort(-q(I3));
delta=I3(ind2);
delta=delta(1:3);
// circbuffer.h: interface for the circbuffer class.
//
//
/////////////////////////////////////////////////////
class circbuffer
{
    public:
    int data[81920];    // Data buffer
    int last21[21];     // Last 21 input values for convolution
    int pointer;        // Current position in circular buffer -continued

APPENDIX A

```
        circbuffer( );
        void addsample(int sample);
        int value (float delay);
        virtual ~circbuffer( );
};
// circbuffer.cpp: implementation of the circbuffer class.
//
//////////////////////////////////////////////////////////
#include "stdafx.h"
#include "circbuffer.h"
//////////////////////////////////////////////////////////
// Construction/Destruction
//////////////////////////////////////////////////////////
#include "math.h"
double reconstruct[201] = { }; //Reconstruction Filter
circbuffer::circbuffer ( ) {
//Clear data buffers
        for (int i=0; i<81920; i++)
                data [i]=0;
        for (i=0; i<21; i++)
                last21[i]=0;
        pointer=0;
        }
//Get the current signal delayed by delay samples
int circbuffer::value(float delay) {
int pntr;
        if (delay<0)
                return(0);
//      Return sample with delay closest to selected delay
        pntr=pointer-floor((delay+0.5)*10);
//      Check for wraparound in circular buffer
        if (pntr<0)
                pntr+=81920;
        return(data[pntr]);
        }
// Add a sample to the buffer
void circbuffer::addsample(int sample) {
        // Shift last 21 values in array (allows faster indexing)
        for (int i=20; i>=1; i--)
                last21[i]=last21[i-1];
        last21[0]=sample;
        for (i=0; i<10; i++) {
                pointer=(pointer+1)%81920;
                double temp=0;
                // Sparse Convolution (only multiply non-zero values of
                // upsampled signal
                for (int j=i; j<=200; j+=10) {
                        temp+=last21[j/10]*reconstruct[j];
                }
                data[pointer]=temp;
        }
}
Logical Statement of Selection
        if ($\epsilon_o$ < 10 and $\epsilon_\alpha$ < 10) {
                $\Delta_n = \Delta_{n-1}$
                }
        else {
                // Check for advantage in shifting by 0.1 samples
                if ($\epsilon_{c+}<\epsilon_\alpha$) {
                        $\Delta_n = \Delta_{n-1} + 0.1$
                        $\epsilon_c=\epsilon_{c+}$
                        }
                if ($\epsilon_\alpha<\epsilon_c$) {
                        $\Delta_n = \Delta_{n-1} - 0.1$
                        $\epsilon_c=\epsilon_{c+}$
                        }
                $\epsilon_c = \epsilon_c /5$    // Scale down current error by 5
                // Check errors for new delays suggested by correlator
                if ($\epsilon_{\delta 1}<\epsilon_c$) {
                        $\Delta_n = \delta_1$
                        $\delta_c=\epsilon_{\delta 1}$
                        }
                if ($\epsilon_{\delta 2}<\epsilon_c$) {
                        $\Delta_n = \delta_2$
                        $\epsilon_c=\epsilon_{\delta 2}$
                        }
                if ($\epsilon_{\delta 3}<\epsilon_c$) {
```

-continued

APPENDIX A

```
                        $\Delta_n = \delta_3$
                        $\epsilon_c=\epsilon_{\delta 3}$
                        }
                if ($\epsilon_0<\epsilon_\alpha$) {
                        $\Delta_n = -1$     //Flag for no cancellation
                        $\epsilon_c=\epsilon_o$    //Turn off ouput of delay line
                        }
                }
```

I claim:

1. An improved patient comfort, magnetic resonance imaging noise cancellation system comprising:
a magnetic resonance imaging system;
a patient mounted pneumatic headset system;
an error microphone connected to said patient mounted pneumatic headset measuring an acoustic noise signal at an ear of said patient; and
a noise cancellation processor producing an acoustic noise signal canceling waveform, said acoustic noise signal canceling waveform being a delayed and inverted acoustic noise signal output from said error microphone.

2. The improved patient comfort, magnetic resonance imaging noise cancellation system of claim 1 wherein said patient mounted pneumatic headset system further comprises:
a patient mounted head band;
a left and right rigid ear cup connected to said head band;
sound-absorbent material-filled soft ear cups;
plastic tubing connected to said ear cup; and
a pneumatic headphone driver generating acoustic signals transmitted through said plastic tubing.

3. The improved patient comfort, magnetic resonance imaging noise cancellation system of claim 1 wherein said error microphone further comprises a pneumatic headphone mounted non-magnetic transducer.

4. The improved patient comfort, magnetic resonance imaging noise cancellation system of claim 3 wherein said pneumatic headphone mounted non-magnetic transducer comprises non-magnetic microphones.

5. The improved patient comfort, magnetic resonance imaging noise cancellation system of claim 3 wherein said pneumatic headphone mounted non-magnetic transducer comprises a piezoelectric microphone.

6. The improved patient comfort, magnetic resonance imaging noise cancellation system of claim 1 wherein said noise cancellation processor comprises
means for isolating said MRI noise signal from said error signal;
an auto-correlator and delay selection algorithm that selects three sample delays reflecting the repetition rate of said MRI noise signal;
an error detector subsystem that determines which delay from said auto-correlator results in the smallest residual noise signal;
an upsampling delay line receives an output from said error detector and delays said noise signal;
an inverse headphone filter processing an output of said upsampling delay line and correcting for the spectral characteristics of headphone transducers and propagation path to said error microphones;
an inverse headphone filter output signal inverter, an output signal from said inverter transmitted to ears of said patient, and a headphone filter.

7. The improved patient comfort, magnetic resonance imaging noise cancellation system of claim 6 wherein said noise cancellation processor further comprises an operator microphone and patient music system.

8. The improved patient comfort, magnetic resonance imaging noise cancellation system of claim 6 wherein said noise cancellation processor further comprises an adder, said adder adding operator instructions to an output of said upsampling delay line.

9. The improved patient comfort, magnetic resonance imaging noise cancellation system of claim 6 wherein said noise cancellation processor 6 further comprises a patient music system providing a music audio signal to an output of said upsampling delay line.

10. The improved patient comfort, magnetic resonance imaging noise cancellation system of claim 6 wherein said upsampling delay line further comprises:

means for upsampling the signal by a preselected factor;

a reconstruction filter convolving the upsampled signal using sparse resolution; and storing the output of said reconstruction filter in a circular buffer.

11. The noise cancellation processor of claim 6 wherein said error detector subsystem further comprises an error metric algorithm that evaluates three delay values output from said auto-correlator, said error metric mathematically defined as $$\varepsilon(n, \delta) = \sum_{k=0}^{127} (x[n-k] - x[n-k-\delta])^2$$

where n is the current sample number and $\delta$ is the desired delay.

12. An improved patient comfort, delay based active noise cancellation method for magnetic resonance imaging comprising the steps of:

measuring an acoustic noise signal at an ear of said patient undergoing magnetic resonance imaging;

selecting three delay values representing a repetition of said acoustic noise signal using an auto-correlation algorithm;

comparing an acoustic noise signal with each of said three delay values from said selecting step with said acoustic noise signal and selecting a delay that produces a most effective noise cancellation waveform;

inverting said noise cancellation waveform selected in said comparing step; and communicating said noise cancellation waveform from said inverting step to said patient using pneumatic headphones thereby canceling the acoustic noise signal received by said patient.

13. The improved patient comfort, delay based active noise cancellation method for magnetic resonance imaging of claim 12 further comprising the step of adding operator instructions and an acoustic music signal to said noise canceling waveform signal after said comparing step.

14. The improved patient comfort, delay based active noise cancellation method for magnetic resonance imaging of claim 12 wherein said measuring step further comprises the steps of:

providing a patient with pneumatic headphones having earcups situated on left and right ears;

including a microphone within said earcups of said pneumatic headphones to measure the acoustic noise signal;

isolating said acoustic noise signal from said including step from any error signals.

15. The improved patient comfort, delay based active noise cancellation method for magnetic resonance imaging of claim 14 wherein said including step further includes including a piezoelectric microphone within said earcups of said pneumatic headphones; and selecting three delay values representing a repetition of said acoustic noise signal using an auto-correlation algorithm.

16. The improved patient comfort, delay based active noise cancellation method for magnetic resonance imaging of claim 12 wherein said selecting step further comprises the steps of:

examining the periodicity of previous $2^N$ samples of an MRI noise signal from said measuring step using an auto-correlation system;

processing a fast fourier transformation of the absolute value of each of said $2^N$ samples from said examining step resulting in a discrete fourier transformation of each sample;

multiplying discrete fourier transform coefficients of each sample by their complex conjugates;

processing an inverse fast fourier transformation of an output from said multiplying step and generating an absolute correlation signal;

selecting indices corresponding to the local maxima of said absolute correlation signal;

sorting the indices from said selecting step in decreasing order of magnitude and selecting indices corresponding to the largest values;

reselecting indices corresponding to the local maxima from said sorting step; and assigning indices of the three largest values to three output delays, said three delays corresponding to the delays most likely to minimize the residual noise signal.

17. The improved patient comfort, delay based active noise cancellation method for magnetic resonance imaging of claim 16 wherein said examining step further comprises the steps of:

upsampling said acoustic noise signal by a factor of 10;

convolving the upsampled signal with a reconstruction filter using sparse convolution; and storing previous $10*2^{N-1}$ samples of said upsampled signal in a circular buffer, said samples retrievable by choosing the proper index of the circular buffer; and comparing an acoustic noise signal with each of said three delay values from said selecting step with said acoustic noise signal and selecting a delay that produces a most effective noise cancellation waveform.

18. The improved patient comfort, delay based active noise cancellation method of claim 12 wherein said comparing step further comprises the steps of:

determining the energy in the error signal over a previous number of samples by calculating iterations of the error metric $$\varepsilon(n, \delta) = \sum_{k=0}^{127} (x[n-k] - x[n-k-\delta])^2 \quad (1)$$

* * * * *

UNITED STATES PATENT AND TRADEMARK OFFICE
CERTIFICATE OF CORRECTION

PATENT NO. : 6,463,316 B1
DATED : October 8, 2002
INVENTOR(S) : Douglas S. Brungart It is certified that error appears in the above-identified patent and that said Letters Patent is hereby corrected as shown below:

Column 2,
Line 51, "Hertzl" should read -- Hertz] --.

Column 4,
Line 40, "a patient" should begin a new paragraph.

Column 7,
Line 32, "$\Delta_{n\text{-}\Delta c}$" should read -- $\Delta_n\text{-}\Delta_c$ --.

Column 8,
Line 26, "I," should read -- $I_1$ --.
Line 27, "AR" should read -- All --.
Line 55, "A" should read -- $\Delta$ --.

Column 9,
Line 48, "The basis" should begin a new paragraph.
Line 58, "delays" should read -- delay --.

Column 9, line 43-Column 10, line 43,
All occurrences of "$\in$" should read -- $\varepsilon$ --.

Signed and Sealed this

Twenty-fifth Day of May, 2004

JON W. DUDAS
*Acting Director of the United States Patent and Trademark Office*